(12) United States Patent
Gebicki et al.

(10) Patent No.: US 11,872,023 B2
(45) Date of Patent: Jan. 16, 2024

(54) METHOD OF ASSESSMENT OF MICROCIRCULATION OSCILLATIONS AND DEVICE THEREFOR

(71) Applicant: Angionica SP. Z O.O., Lodz (PL)

(72) Inventors: Jerzy Gebicki, Lodz (PL); Andrzej Marcinek, Lodz (PL)

(73) Assignee: ANGIONICA SP. Z O.O., Lodz (PL)

( * ) Notice: Subject to any disclaimer, the term of this patent is extended or adjusted under 35 U.S.C. 154(b) by 610 days.

(21) Appl. No.: 17/050,079

(22) PCT Filed: Apr. 23, 2019

(86) PCT No.: PCT/EP2019/060305
§ 371 (c)(1),
(2) Date: Oct. 23, 2020

(87) PCT Pub. No.: WO2019/206869
PCT Pub. Date: Oct. 31, 2019

(65) Prior Publication Data
US 2021/0236005 A1 Aug. 5, 2021

(30) Foreign Application Priority Data

Apr. 26, 2018 (EP) ..................................... 18461551

(51) Int. Cl.
*A61B 5/00* (2006.01)
*A61B 5/026* (2006.01)

(52) U.S. Cl.
CPC .................................. *A61B 5/0261* (2013.01)

(58) Field of Classification Search
CPC ........................... A61B 5/0261; A61B 5/0071
See application file for complete search history.

(56) References Cited

U.S. PATENT DOCUMENTS

2012/0310057 A1* 12/2012 Gebicki ............. A61B 5/14546
600/317

FOREIGN PATENT DOCUMENTS

WO 2012164495 A1 12/2012

OTHER PUBLICATIONS

PCT International Search Report in PCT/EP2019/060305 dated May 24, 2019, 4 pages.

(Continued)

*Primary Examiner* — Rajeev P Siripurapu
(74) *Attorney, Agent, or Firm* — BROWDY AND NEIMARK, P.L.L.C.

(57) ABSTRACT

A method of assessment of microcirculation oscillations comprises illumination of a selected location on non-hairy skin of a human subject in a resting steady condition without any blockage or stimulation of the blood flow with exciting light capable of inducing skin NADH fluorescence signal for a period of time; simultaneously with said illumination detecting, measuring and recording as a function of time the induced NADH fluorescence signal emitted from the said selected location to obtain the time course of the NADH fluorescence signal intensity in the said period of time; and computer implemented steps of: fitting of a baseline about which the NADH fluorescence signal oscillates to the said time course of the NADH fluorescence signal; and determination of a mean squared error of the deviation of the NADH fluorescence signal from the fitted baseline as a parameter of oscillatory function of the skin microcirculation.

10 Claims, 5 Drawing Sheets

(56) References Cited

OTHER PUBLICATIONS

Piotrowski, L., et al., "Note: Flow mediated skin fluorescence—A novel technique for evaluation of cutaneous microcirculation", Review of Scientific Instruments, AIP, vol. 87, No. 3, 036111, (Mar. 30, 2016).

Tarnawska, Maria, et al., "A pilot study with flow mediated skin fluorescence: A novel device to assess microvascular endothelial function in coronary artery disease", Cardiology Journal, vol. 25, No. 1, pp. 120-127, Feb. 27, 2018.

\* cited by examiner

METHOD OF ASSESSMENT OF MICROCIRCULATION OSCILLATIONS AND DEVICE THEREFOR

CROSS REFERENCE TO RELATED APPLICATIONS

This is a National Phase entry of International Application No. PCT/EP2019/060305, filed Apr. 23, 2019, the disclosure of which is incorporated herein by reference in its entirety.

FIELD OF THE INVENTION

The invention relates to a method of assessment of microcirculation oscillations (flowmotion) and a system or device for assessment of microcirculation oscillations.

PRIOR ART

Natural and spontaneous phenomenon observed in the vascular networks both in vitro and in vivo is so called vasomotion, i.e. rhythmic oscillations of vascular tone that is generated within a vascular wall. Vasomotion is caused by local changes in smooth muscle constrictions and dilations and is not a consequence of heartbeat, respiration or neuronal input (H. Nillson et al., Vasomotion: Mechanisms and Physiological Importance, Molecular Interventions, March 2003, Volume 3, Issue 2, pp. 79-89). Vasomotion is responsible for rhythmic variations (oscillations) of blood flow pressure and flow, also called flowmotion.

Microcirculation is the part of the circulation system having very important physiological function. Microcirculation vessels ensure efficient diffusion-limited exchange of gases, metabolites and elements of the immune system between blood and extravascular aqueous space as well as efficient humoral and thermal regulation.

Microcirculation is mostly studied in humans at the level of skin, i.e. as a skin microcirculation. Although rhythmic motions of vessel wall and triggered by them changes of blood flow are seen in the whole vascular bed, their visualization and recording are especially easy in the vasculature of the skin. Skin microcirculation vasomotion is the rhythmic variation of the skin microvessel diameter and is responsible for the skin microcirculatory blood flow oscillations, i.e. the skin blood flowmotion. Functional impairment (dysfunction) of the microcirculatory function of many regions, tissues and organs, including impairment of natural and spontaneous blood flow oscillations plays very important role in pathophysiology of many diseases, especially such as vascular diseases and hypertension. As skin microcirculation impairment mirrors impairments in other regions, the analysis of microcirculatory blood flow oscillations or the skin blood flowmotion has a diagnostic value.

Microcirculatory blood flow has been up to now investigated indirectly in humans at the level of skin by means of laser Doppler flowmetry/fluximetry (LDF) and spectral Fourier analysis (transformation) of skin LDF signal from flow/flux variations in the time domain into frequency spectrum. (M. Rossi, Diagnostic values of skin vasomotion investigation in vascular diseases, Advances in Biomedical Research, in Proc. International Conference on Medical Physiology, pp. 374-380, 2010). Assessment of microcirculatory function by LDF is performed both under resting conditions and during flow changes induced by ischemia, heating or administration of vasoactive substances.

Other optical methods like photoplethysmography (PPG), pulse oximetry, and diffuse reflection spectroscopy rely on the blood absorption and reflection of light by blood to estimate the blood volume and oxygen saturation. They give no information about the blood flow.

LDF method is virtually the only existing method of non-invasive investigation of microcirculation and is based on the utilization of the Doppler shift arising when the laser light is scattered by a red cell moving in the microvessels. However, it has certain disadvantages, i.e. high cost, uncertainty and variability of obtained measurements, troublesome intra- and interindividual comparison.

A testing method is needed that would allow to investigate and assess microcirculation flowmotion (oscillations) function and detect any dysfunctions at an early stage of impairment in order to identify patients for further more detailed and complicated diagnostic tests and/or for prophylactic or therapeutic intervention to improve the function.

The need exists to provide a non-invasive test for investigating and assessing microcirculation flowmotion (oscillations) function which would be reliable, easy to carry out and inexpensive, and capable of objective standardization and thus applicable for tests in large patient populations, for example for screening purposes.

There is also a need for a simple, quick and non-expensive test that would allow to monitor and control the response of a patient to a medical treatment of a disease, such as cardiovascular disease.

It has now been found that measurement of skin NADH fluorescence in resting conditions, that is without any mechanical, physical or pharmacological blockage and release of blood flow can be successfully used for the assessment of spontaneous skin microcirculation oscillations (flowmotion).

SUMMARY OF THE INVENTION

The invention provides a method of assessment of oscillatory function of the skin microcirculation and a method of determination of a parameter for assessment of oscillatory function of the skin microcirculation, as well as a device or system therefor, the method comprising:
  illumination of a selected location on non-hairy skin of a human subject in a resting steady condition without any blockage of the blood flow with exciting light capable of inducing skin NADH fluorescence signal for a period of time;
  simultaneously with said illumination detecting, measuring and recording as a function of time an induced NADH fluorescence signal emitted from the said selected location to obtain the time course of the NADH fluorescence signal intensity in the said period of time; and
  computer implemented steps of:
    fitting of a baseline about which the NADH fluorescence signal oscillates to the said time course of the NADH fluorescence signal intensity; and
    determination of a mean squared error of the deviation of the NADH fluorescence signal from the fitted baseline as a parameter of oscillatory function of the skin microcirculation.

Definition of a parameter of assessment in the method of the invention as the mean squared error of the deviation of the NADH fluorescence signal from the fitted baseline makes this parameter an objective, operator-independent, and patient-specific result of the test. Such a characteristic of the parameter allows its easy standardization.

Time-course of NADH fluorescence intensity signal allows to obtain important data for analysis of microcirculation dysfunctions.

BRIEF DESCRIPTION OF THE FIGURES OF DRAWING

DETAILED DESCRIPTION OF THE INVENTION

Figure 1:
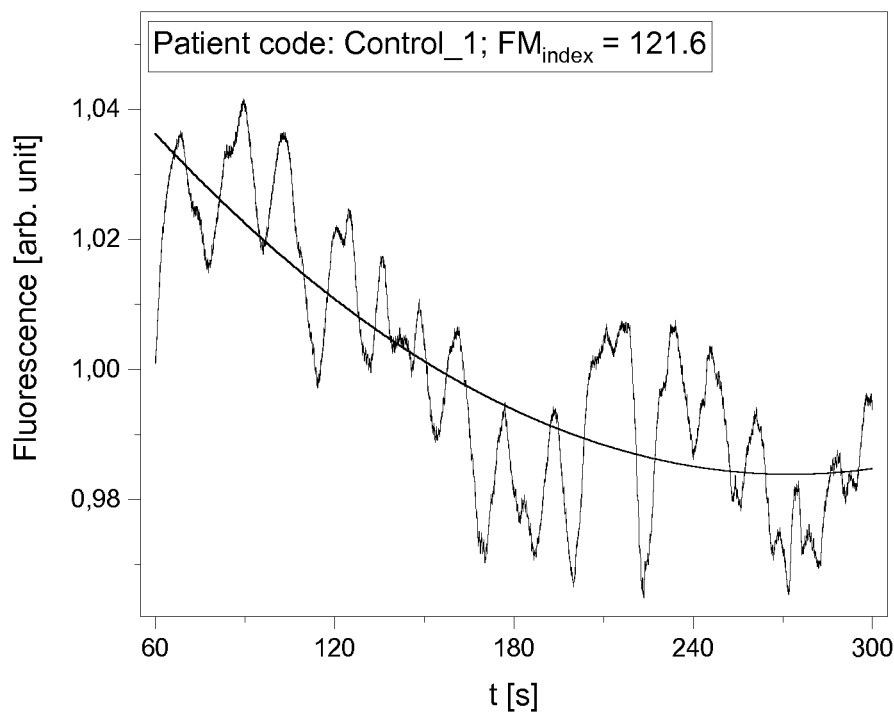
FIGS. 1 to 4 show recorded time courses of flow-mediated skin NADH fluorescence and fitted baselines in apparently healthy human subject—volunteers.

The present invention provides a method of assessment of oscillatory function of the skin microcirculation in a human subject, the method comprising:
illumination of a selected location on non-hairy skin of a human subject in a resting steady condition without any blockage or stimulation of the blood flow with exciting light capable of inducing skin NADH fluorescence signal for a period of time;
simultaneously with said illumination detecting, measuring and recording as a function of time an induced NADH fluorescence signal emitted from the said selected location to obtain the time course of the fluorescence signal intensity in the said period of time; and
computer implemented steps of:
fitting of a baseline about which the NADH fluorescence signal oscillates to the said time course of the fluorescence signal intensity; and
determination of a mean squared error of the deviation of the NADH fluorescence signal from the fitted baseline as a parameter of oscillatory function of the skin microcirculation.

The present invention provides also a method of determination of a parameter of oscillatory function of the skin microcirculation in a human subject, the method comprising:
illumination of a selected location on non-hairy skin of a human subject in a resting steady condition without any blockage or stimulation of the blood flow with exciting light capable of inducing skin NADH fluorescence signal for a period of time;
simultaneously with said illumination detecting, measuring and recording as a function of time an induced NADH fluorescence signal emitted from the said selected location to obtain the time course of the fluorescence signal intensity in the said period of time; and
computer implemented steps of:
fitting of a baseline about which the NADH fluorescence signal oscillates to the said time course of the fluorescence signal intensity; and
determination of a mean squared error of the deviation of the NADH fluorescence signal from the fitted baseline as a parameter of oscillatory function of the skin microcirculation.

The method of the invention utilizes so-called flow-mediated skin fluorescence. The method is known, for example from Hellman et al., Microvascular Research 113 (2017), 60-84; Piotrowski et al. Review of Scientific Instruments, AIP, Melville, N.Y., USA, vol. 87, no. 3 (2016); Tarnawska et el., Cardiology Journal, vol. 25, no. 2 (2018, 120-127; and WO2012/164494 in the application for determination of certain quantitative parameters of changes of skin NADH fluorescence signal mediated by blocking (ischemia) and then releasing (hyperemia) the blood flow in the artery. Ischemic (low flow) and hyperemic (high flow) responses give the information about the condition of vascular endothelium. Different ischemic and hyperemic responses were obtained between healthy subjects and patients with cardiovascular disease (CAD), a population with well characterized microvascular dysfunction. Oscillations of the time-course of skin NADH fluorescence was neither considered nor determined in the above method.

Oscillations of the time-course of skin NADH fluorescence in the method of the invention mirror the skin microcirculatory blood flow oscillations.

The data obtained in the method of the invention can be used in the early diagnostics of microcirculation dysfunction.

The method of the invention comprises illumination of a non-hairy skin surface of a human subject in one selected location. Said non-hairy skin surface means inter alia the surface of the upper limb of the subject, such as forearm, hand or a finger, preferably the forearm. Such a non-hairy skin surface includes also the surface of the lower limb, such as thigh and feet. Such a non-hairy skin surface includes also for example the forehead area.

However, as the method requires measurement of skin fluorescence signal in a resting conditions and steady motionless state of a patient, the most preferred location of illumination is the forearm, as it allows that patient be seated comfortably motionless during the test.

Illumination in one selected location should be understood as illumination wherein illumination means is directed onto one single position/location on the surface of the skin and is not intentionally moved with respect to this position/location.

It will be appreciated by a skilled person that flow-mediated skin fluorescence signal is emitted from the skin when the skin is illuminated with exciting light and during such illumination.

It should be understood that any mention herein of a fluorescence signal relates to the NADH fluorescence signal emitted by the skin of a subject.

It will be appreciated by a skilled person that exciting light capable of inducing NADH fluorescence will have the wavelength at the UV range absorbed by NADH. NADH absorbs light at almost the entire UVA spectrum in the range from 300 to 400 nm and in response to illumination emits fluorescence light at the range of 400 nm to 600 nm, with a maximum at about 460 nm.

Preferably, exciting light will have the wavelength at about 350 to 360 nm, especially 360 nm.

Preferably, emitted fluorescence light will be detected and measured at the wavelength in the range from 420 nm to 480 nm, especially about 460 nm.

The period of time during which the detection, measurement and recording of the fluorescence signal is performed is the period that allows to obtain sufficient evaluation of the fluorescence changes for computer implemented fitting of a baseline. Such sufficient period of time generally should be at least one minute, such as 1 to 5 minutes, such as 1, 2, 3, 4 or 5 minutes. Period of measurement can be longer than 5 minutes, such as up to 10 minutes.

Preferably, results of measurement are normalized with respect to the mean value of the fluorescence signal in the central period of measurement.

It should be understood that for performing computer implemented steps as defined above a computer program is used. It is advantageous to reject initial section of the measurement. For example, if the period of time of measurement is 5 minutes, then initial 1-minute section is rejected and period of measurement entailing second to fifth minutes, inclusive, is taken for fitting the baseline and determination of the mean squared error.

It should be understood that fitted baseline about which NADH fluorescence signal oscillates is an artificially generated/created line. Fitting of a baseline about which NADH fluorescence signal oscillates can be performed using polynomial regression method.

On the basis of the courses of flow-mediated skin fluorescence collected for the group of patients and a control group it has been found that a baseline about which the fluorescence signal oscillates is not horizontal and can be an ascending, descending, ascending reaching plateau, descending reaching plateau, parabolic, etc., one.

Preferably, on the basis of such courses of a baseline second order polynomial regression method is used for fitting the baseline since it has the best fit to the changes in the course of fluorescence signal not related to the blood flow oscillations.

Polynomial, preferably second order polynomial is fitted to experimental points using linear regression method (least squares method). Such fitting is unique, as a result of the solution of the system of equations. For parabola it is a system of 3 equations that allow to find a unique parameters of the equation y=intercept+B1*x+B2*x^2.

In the least squares method the best fit is considered the one wherein sum of squares of deviations of the experimental point from polynomial function, i.e. SSE=Σ(yi−Yi)^2 (residual sum of squares) is minimal (yi—experimental points, Yi—corresponding points on the fitted curve). At the same time, SSE value is the measure of the fitting error (deviation of the points from polynomial relationship).

In the case of analysis of oscillations, deviation of the fluorescence signal can used as an assessment of oscillations measure; a parameter that is objective and patient specific result of the test.

In statistical analysis squared deviation (residual sum of squares) can be normalized with respect to the number of analyzed experimental points (the time of measurement of oscillations taken for analysis). That is, the mean squared error is calculated.

Mean squared error is defined as:

MSE=SSE/(n−m), where
SSE is the residual sum of squares
n is the number of measurement points taken for analysis (it depends on the time interval and sampling frequency),
m is the number of regression parameters describing polynomial (3 in the case of second order polynomial).

MSE is unbiased estimator of deviation of the points/signals from the polynomial relationship. This allows comparison of the results obtained from observation of oscillations in different time intervals.

Defining oscillations parameter as MSE makes it objective, operator independent, characteristic for a patient and his testing with the method of flow-mediated skin fluorescence.

The present inventors have chosen to call the parameter thus defined in the tests described in the Examples that follow a Flowmotion index. However, it is not limiting as it may be given any other name.

The present invention provides also a device or system for performing the method of the invention as defined above.

The device or system for assessment of oscillatory function of the skin microcirculation or determination of a parameter of such function in a human subject according to the invention comprises:
a means for illumination of a skin of said subject with exciting light capable to induce NADH fluorescence signal;
a means for detecting and measuring NADH fluorescence signal emitted from the skin during such illumination;
a processing unit which is configured to perform the following:
receiving and recording the course of said NADH fluorescence signal in time,
fitting a baseline about which the NADH fluorescence signal oscillates to the said time course of the fluorescence signal intensity, and
determination of a mean squared error of the deviation of the NADH fluorescence signal from the fitted baseline as a parameter of oscillatory function of the skin microcirculation
and
a means for displaying a result of determination of the said parameter of oscillatory function.

The device or system according to the invention may also comprise a means for attaching a portable memory to retrieve and save the said course of the fluorescence signal against time for it to be printed and its pattern analyzed.

Techniques of obtaining, detecting, measuring and recording NADH fluorescence signal from tissue cells (NADH fluorometry) as well as fluorometers are as such well known in the art and can be used to perform the method of the invention and in the device/system of the invention.

Said means for illuminating, detecting, measuring, recording and performing computer-implemented steps can be integrated in such a fluorometer.

Said illumination means will be a source of excitation light capable of emitting UV light in the range absorbed by NADH, i.e. at the wavelength range of 300 to 400 nm.

Said means for detecting will be a detector of fluorescence signal at least in the range emitted by NADH, i.e. at the wavelength range of 400 to 600 nm, preferably 420 nm to 480 nm, especially about 460 nm.

Said illumination and detecting means preferably are combined in a single measuring head to be placed at the selected location close to the skin of the subject. Such a measuring head will also have measurement window and can also comprise interference filters.

Generally, there is a certain flexibility in configuration of the device, provided that all essential elements listed above are included.

Conventional light sources of excitation light known in the art can be used, including filtered spectral lamp such as mercury or xenon lamp, light emitting diode LED, laser diode or pulsed laser. Advantageous light source is the light emitting diode LED.

Conventional detectors can be used, such as photodiode detector, fast photodiode detector, photon multiplier tube, etc.

The exciting light can be carried out to the skin through the window of the measuring head placed close to the skin, either in direct contact with the skin or in close vicinity to the skin. The emitted skin fluorescence can be collected through the same window of the measuring head.

The measuring head can be connected to the light source and detector through the light guide or it can comprise of both light source and detector in one arrangement.

Any conventional light guide can be used for carrying excitation light and for collecting fluorescence light, such as optical fibers, optionally in a flexible housing.

In one embodiment, the measurement will be performed on a forearm or the palmar side of a hand and the measuring head will be attached to the support for placing hand or to the band fixed on the hand.

In another embodiment, the measurement will be performed on the dorsal side of a hand placed on a support, such as tripod, and the measuring head will be fixed above the hand.

In another embodiment, the measurement will be performed on a finger, by means of a cup, a hoop or a cuff at the end of the measuring head, said cup, hoop or cuff being tightened around the finger depending on the size of the latter.

In yet another embodiment the measurement will be performed in a multi-point manner. For example, several light-guides can be carried to the band mounted around a forearm or a finger.

Example

NADH fluorescence from skin cells of the hand of a human subject and changes of intensity of this fluorescence in time was measured.

The measurement was performed using prototype device equipped with a measuring head comprising of a light emitting diode LED, photodiode detector, interference filters in one arrangement attached to the armrest with the optical window suitable for measuring the emission from the surface of the skin.

The wavelength of the excitation light was 340 nm and the wavelength of monitored emission signal was 460 nm.

Intensity of a fluorescence signal from the hand of the subject freely placed on an armrest without any stimulation of circulation was collected and recorded for 5 minutes.

The measurements were performed in apparently healthy volunteers as a control as well as in the group of oncological patients. The course of florescence signal in time was recorded and plotted against time.

All results were normalized to the mean signal value in the between 2 and 3 minutes of measurement (central measurement period). The mean value of the results from this interval was computed and then fluorescence signals in the whole measurement range is divided by this mean value. In this manner normalized presentation of results is obtained (about the value 1), independently of an individual level of the fluorescence from the skin of a given subject.

For further steps results during first minute of the measurement were rejected. Fitting a baseline was performed for normalized results and mean squared errors (also called here Flow motion index $FM_{index}$) were determined on the basis of normalized results using computer program.

To obtain values in the range ones—hundreds calculated values od $FM_{index}$ were multiplied by $10^6$; obtained values were rounded to decimals.

Oscillatory function parameters were calculated according to the following equation:

$$MSE = SSE/(n-m),$$

where:

SSE—residual sum of squares;

MSE—mean squared error=the residual sum of squares divided by the number of degrees of freedom;

n—the number of measurement points dependent on sampling frequency: here every 40 ms;

m—the number of regression parameters (here second order polynomial, i.e. m=3)

The results are presented in Table 1 (control group of volunteers) and Table 2 (oncological patients). For some subjects several repeated measurements were performed and mean values were determined.

Figure 2:
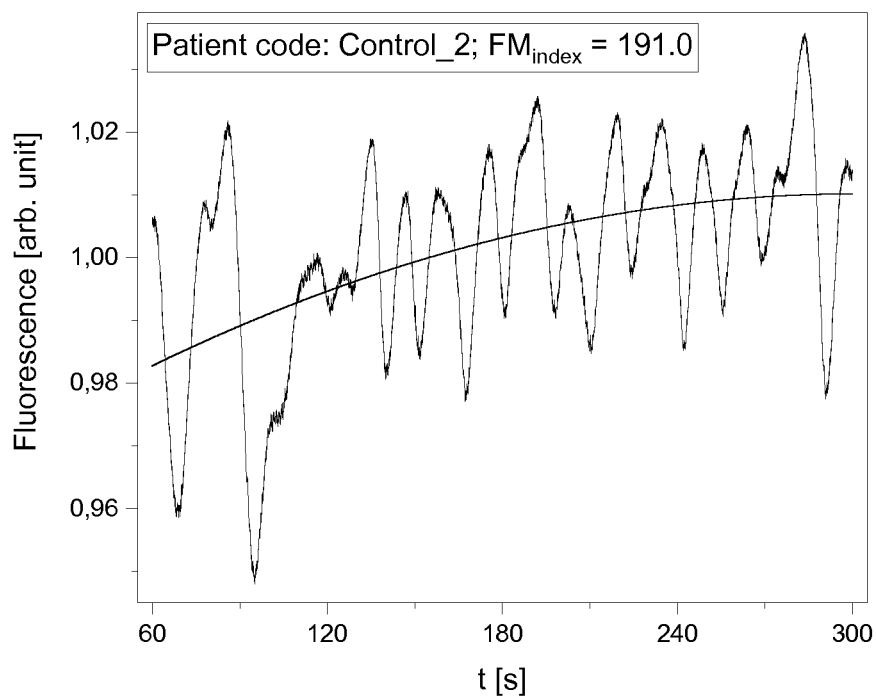
Figure 3:
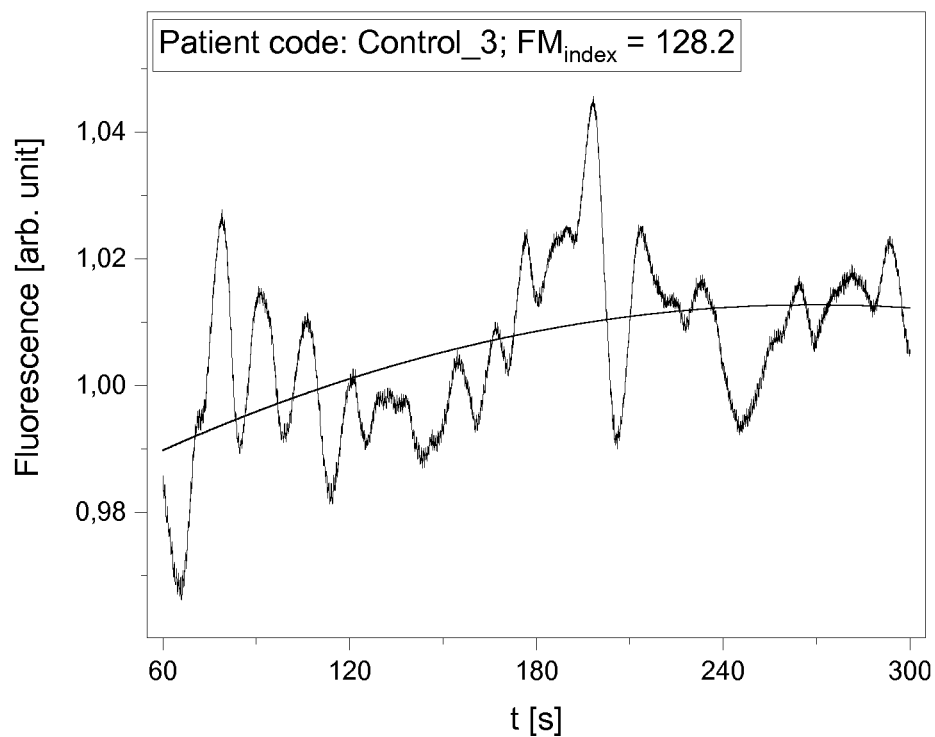
Figure 4:
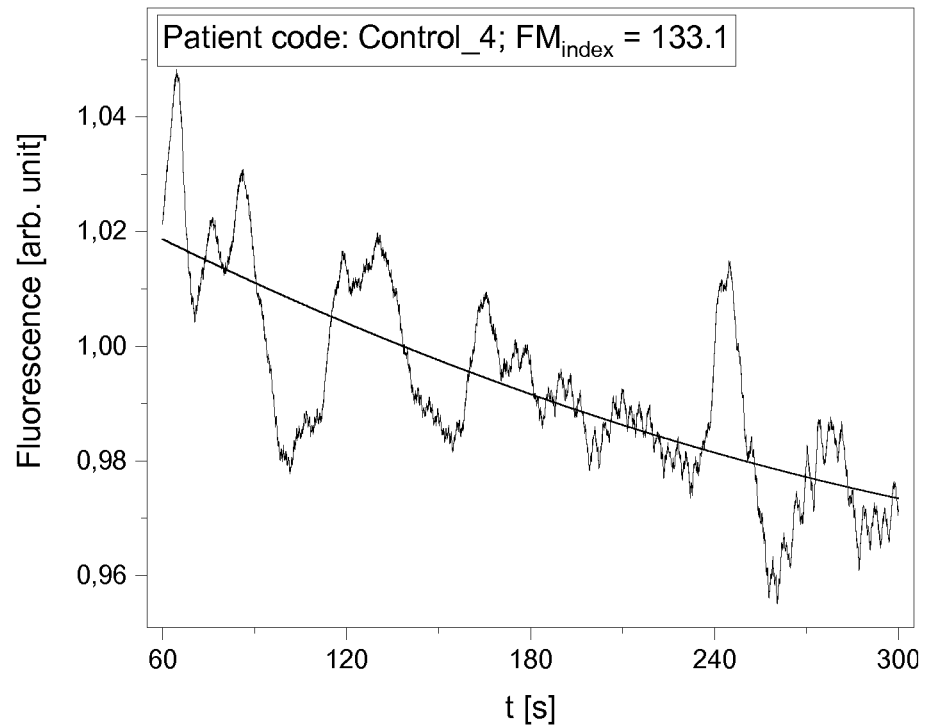
Figure 5:
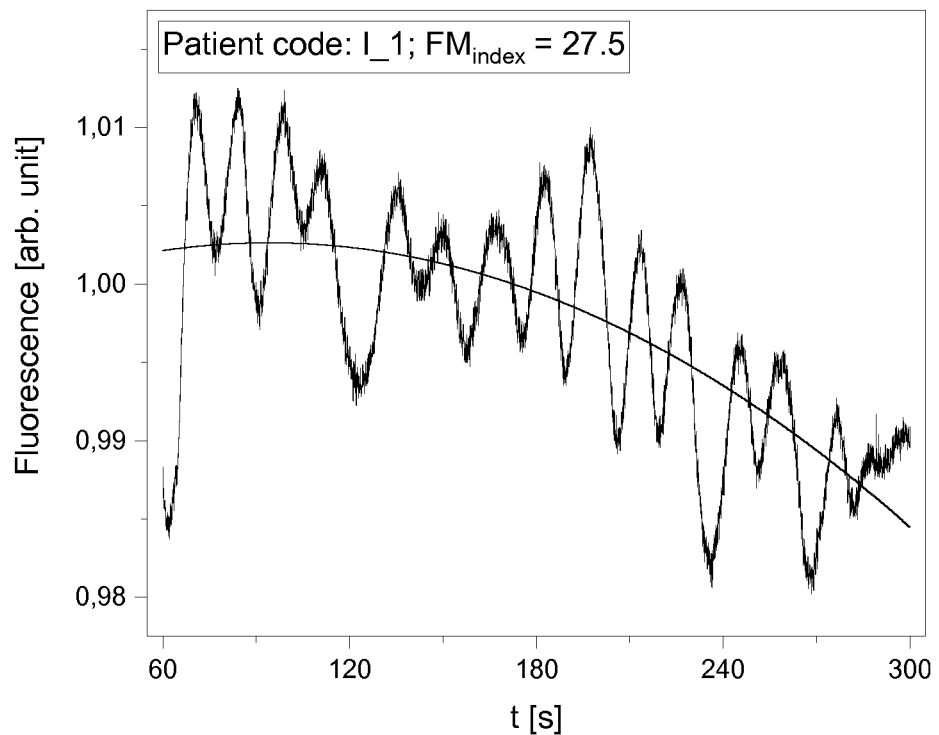
FIGS. 5 to 10 show recorded time courses of flow-mediated skin NADH fluorescence and fitted baselines in patients.
Figure 6:
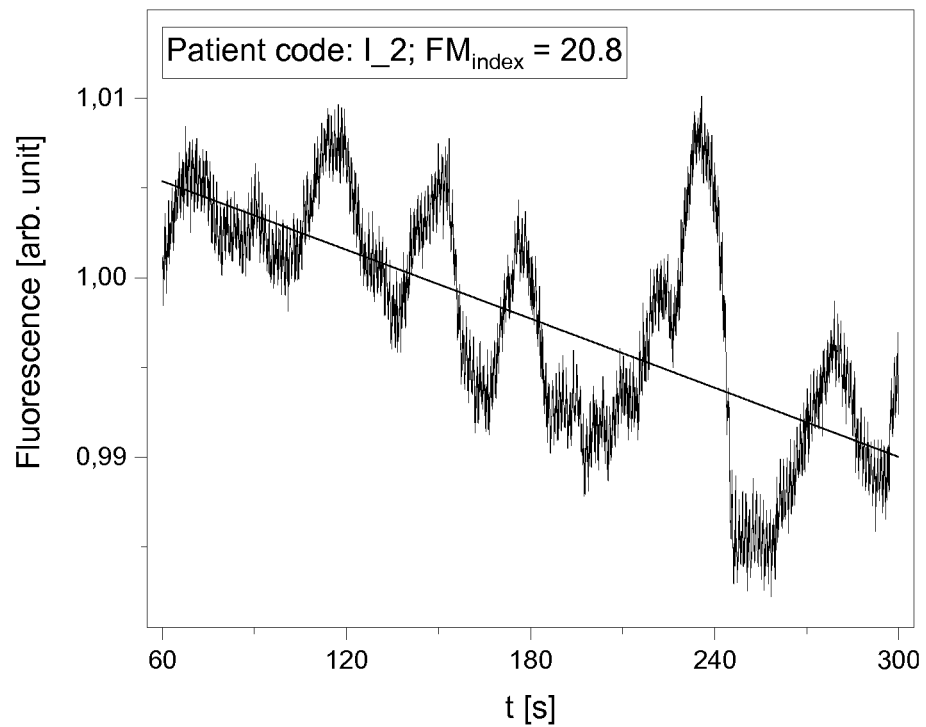
Figure 7:
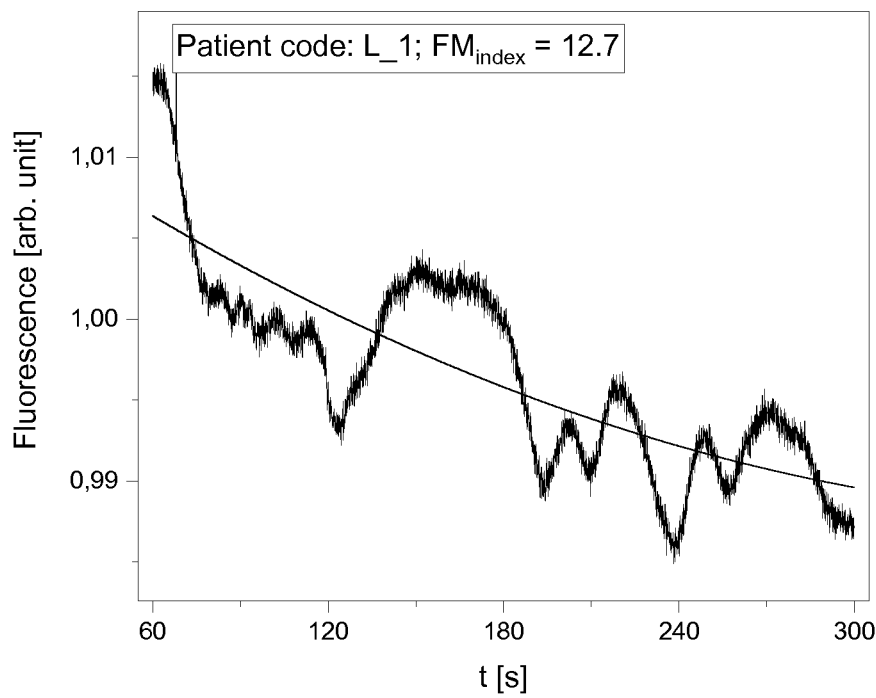
Figure 8:
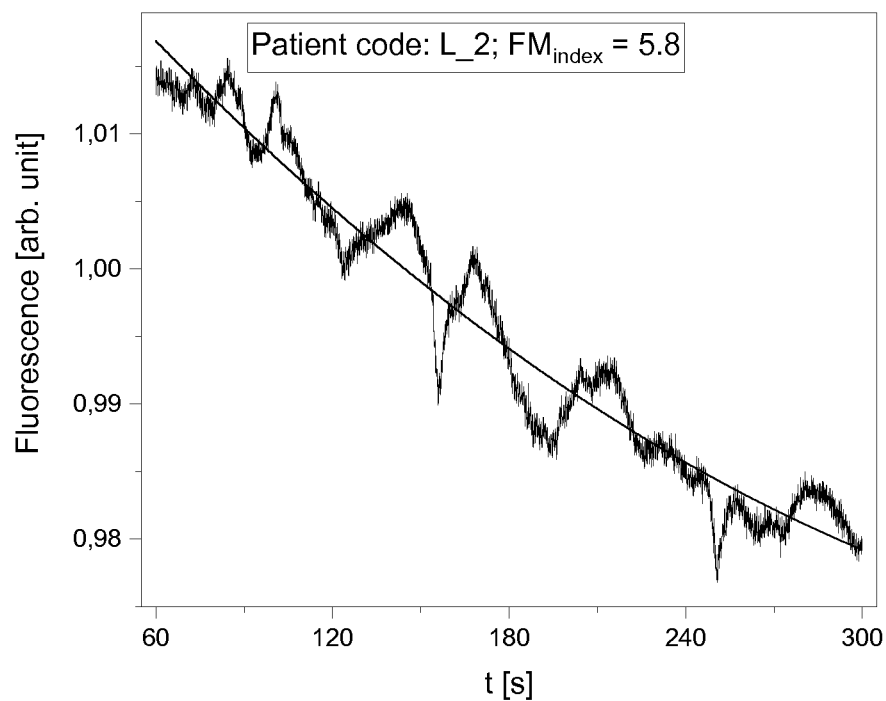
Figure 9:
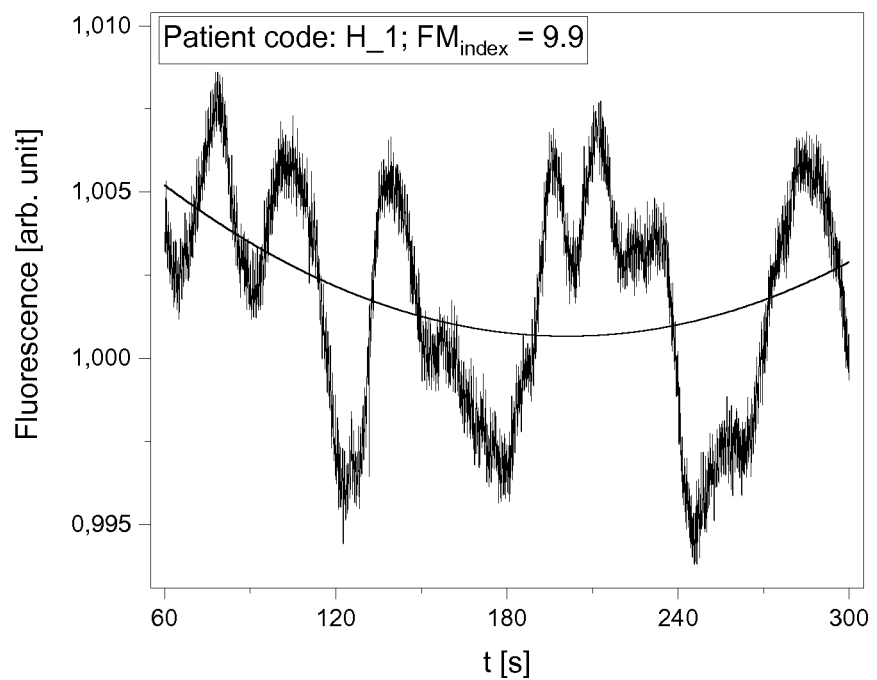
Figure 10:
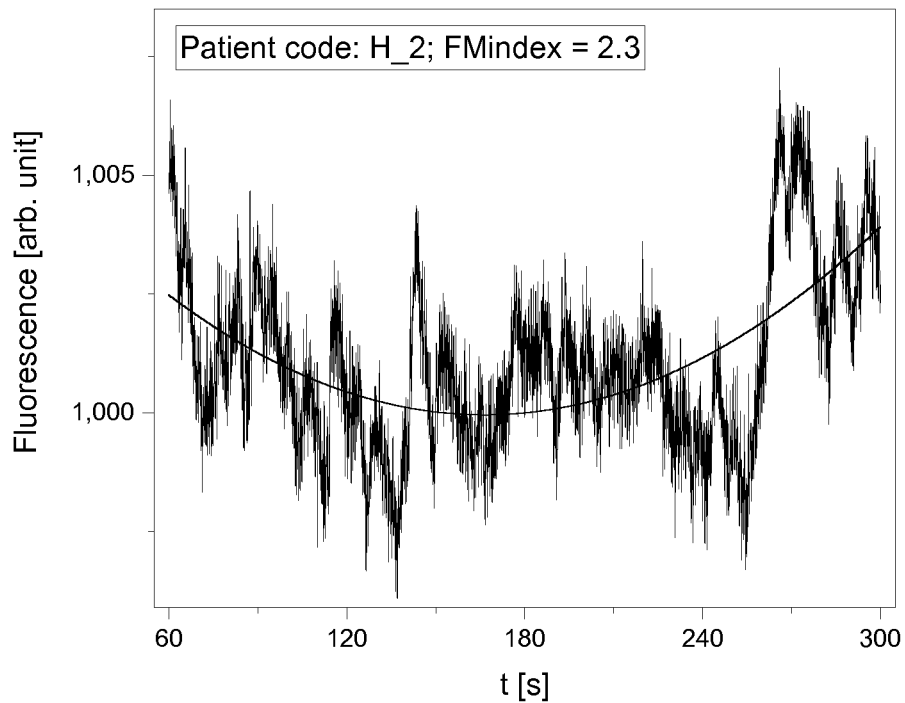

Additionally, time courses of the fluorescence signal with fitted baselines about which signals oscillated were plotted and presented on FIGS. 1 to 4 for control subjects 1, 2, 3 and 4, and in FIGS. 5 to 10 for patients I_1, I_2, L_1, L_2, H_1, and H_2, respectively

TABLE 1

Healthy volunteers-control group

| Subject | $FM_{index}$ | | | | | | mean |
|---|---|---|---|---|---|---|---|
| Control_1 | 121.6 | | | | | | 121.6 |
| Control_2 | 204.8 | 194.6 | 211.0 | 191.0 | 117.9 | 257.6 | 285.7 | 208.9 |
| Control_3 | 128.2 | 138.6 | 63.1 | | | | | 110.0 |
| Control_4 | 221.7 | 133.1 | 60.1 | 26.1 | 155.4 | | | 119.3 |
| Control_5 | 96.1 | 134.7 | 286.1 | | | | | 172.3 |
| Control_6 | 39.3 | 39.4 | 42.9 | | | | | 40.5 |
| Control_7 | 53.7 | 82.2 | 52.2 | | | | | 62.7 |
| Control_8 | 104.0 | | | | | | | 104.0 |

The mean for the whole group was 117.4.

TABLE 2

Oncological patients

| Patient | $FM_{index}$ | Mean |
|---|---|---|
| Patients with intestine cancer | | |
| I_1 | 27.5 | 58.8 |
| I_2 | 20.8 | |
| I_3 | 122.0 | |
| I_4 | 68.9 | |
| I_5 | 10.7 | |
| I_6 | 51.7 | |
| I_7 | 110.1 | |
| Patients with lung cancer | | |
| L_1 | 12.7 | 21.5 |
| L_2 | 5.8 | |
| L_3 | 46.0 | |
| Patients with head cancer | | |
| H_1 | 9.9 | 8.7 |
| H_2 | 2.3 | |
| H_3 | 3.5 | |
| H_4 | 19.0 | |

Statistical analysis: Student's t-distribution with two samples assuming unequal variances.

Variable 1 is the mean of the $FM_{index}$ for control group, Variable 2 is the $FM_{index}$ for the groups of patients.

1. Control versus patients with intestine cancer

| | Variable 1 | Variable 2 |
|---|---|---|
| Mean | 117.4125 | 58.814286 |
| Variance | 2935.36125 | 1919.2748 |
| Observations | 8 | 7 |
| Hypothesized Mean | 0 | |

-continued

1. Control versus patients with intestine cancer

|  | Variable 1 | Variable 2 |
|---|---|---|
| Difference | | |
| df | | 13 |
| t Stat | | 2.314305705 |
| P(T <= t) one-tail | | 0.018822754 |
| T Critical one-tail | | 1.770933396 |
| P(T <= t) two-tail | | 0.037645507 |
| T Critical two-tail | | 2.160368656 |

2. Control versus patients with lung cancer

|  | Variable 1 | Variable 2 |
|---|---|---|
| Mean | 117.4125 | 21.5 |
| Variance | 2935.36125 | 462.09 |
| Observations | 8 | 3 |
| Hypothesized Mean Difference | 0 | |
| df | 9 | |
| t Stat | 4.202203933 | |
| P(T <= t) one-tail | 0.001149589 | |
| T Critical one-tail | 1.833112933 | |
| P(T <= t) two-tail | 0.002299178 | |
| T Critical two-tail | 2.262157163 | |

3. Control versus patients with head cancer

|  | Variable 1 | Variable 2 |
|---|---|---|
| Mean | 117.4125 | 8.675 |
| Variance | 2935.36125 | 58.509167 |
| Observations | 8 | 4 |
| Hypothesized Mean Difference | 0 | |
| df | 8 | |
| t Stat | 5.566792934 | |
| P(T <= t) one-tail | 0.000265216 | |
| T Critical two-tail | 1.859548038 | |
| P(T <= t) one-tail | 0.000530433 | |
| T Critical two-tail | 2.306004135 | |

Despite of small number of tested subjects, virtually all analyses show statistically significant difference (decline of oscillations) with respect to control group. The method possesses significant diagnostic potential.

What is claimed is:

1. A method of assessment of oscillatory function of skin microcirculation, the method comprising:
   illumination of a selected location on non-hairy skin of a human subject in a resting steady condition without any blockage or stimulation of blood flow with exciting light capable of inducing skin NADH fluorescence signal for a period of time;
   simultaneously with said illumination detecting, measuring and recording as a function of time the induced NADH fluorescence signal emitted from the selected location to obtain a time course of the NADH fluorescence signal intensity in said period of time; and
   computer implemented steps of:
      fitting of a baseline about which the NADH fluorescence signal oscillates to the time course of the NADH fluorescence signal; and
      determination of a mean squared error of deviation of the NADH fluorescence signal from the fitted baseline as a parameter of oscillatory function of the skin microcirculation.

2. The method of claim 1, wherein said fitting of the baseline is performed using polynomial regression method.

3. The method of claim 2, wherein second order polynomial regression method is used.

4. The method of claim 3, wherein said fitting is performed using least squares method.

5. The method of claim 1, wherein said period of time is at least 1 minute.

6. The method of claim 1, wherein for said fitting of the baseline an initial period of measurement is rejected.

7. A device for assessment of oscillatory function of the skin microcirculation, the device comprising:
   a means for illumination of a skin of said subject with exciting light capable to induce NADH fluorescence;
   a means for detecting and measuring NADH fluorescence signal emitted from the skin;
   a processing unit which is configured to perform the following:
      receiving and recording time course of intensity of the NADH fluorescence signal,
      fitting of a baseline about which the NADH fluorescence signal oscillates to the time course of the fluorescence signal, and
      determination a mean squared error of deviation of the NADH fluorescence signal from the fitted baseline as a parameter of oscillatory function of the skin microcirculation,
   and
   a means for displaying a result of determination of said parameter of oscillatory function.

8. The device according to claim 7, wherein said fitting of the baseline is performed using polynomial regression method.

9. The device or system according to claim 8, wherein second order polynomial regression method is used.

10. The device according to claim 9, wherein least squares method is used.

* * * * *